(12) United States Patent
Assmann et al.

(10) Patent No.: US 8,841,908 B2
(45) Date of Patent: Sep. 23, 2014

(54) APPARATUS WITH LOCAL COIL ARRANGEMENT AND IMPLANTABLE DEVICE

(75) Inventors: Stefan Assmann, Erlangen (DE); Okan Ekinci, Uttenreuth (DE); Björn Heismann, Erlangen (DE); Reto Merges, Erlangen (DE); Edgar Müller, Heroldsbach (DE); Sebastian Schmidt, Weisendorf (DE)

(73) Assignee: Siemens Aktiengesellschaft, München (DE)

( * ) Notice: Subject to any disclaimer, the term of this patent is extended or adjusted under 35 U.S.C. 154(b) by 503 days.

(21) Appl. No.: 13/104,785

(22) Filed: May 10, 2011

(65) Prior Publication Data

US 2012/0112750 A1    May 10, 2012

(30) Foreign Application Priority Data

May 11, 2010   (DE) .......................... 10 2010 020 152

(51) Int. Cl.
*G01V 3/00*          (2006.01)
(52) U.S. Cl.
USPC .......................................... 324/307; 324/322
(58) Field of Classification Search
USPC ............................ 324/300–322; 600/407–445
See application file for complete search history.

(56) References Cited

U.S. PATENT DOCUMENTS

| | | | |
|---|---|---|---|
| 6,591,138 B1 * | 7/2003 | Fischell et al. ................... | 607/45 |
| 6,600,319 B2 | 7/2003 | Golan | |
| 6,600,945 B2 * | 7/2003 | Ginggen et al. ............... | 600/419 |
| 6,971,391 B1 * | 12/2005 | Wang et al. .................... | 128/846 |
| 7,200,504 B1 * | 4/2007 | Fister ............................... | 702/75 |
| 7,304,477 B2 * | 12/2007 | Konijn et al. ................... | 324/318 |
| 7,313,430 B2 | 12/2007 | Urquhart et al. | |
| 7,417,433 B2 | 8/2008 | Heid et al. | |
| 7,729,758 B2 * | 6/2010 | Haller et al. ....................... | 607/2 |
| 7,738,942 B2 * | 6/2010 | Weiner et al. ................. | 600/411 |
| 7,819,826 B2 * | 10/2010 | Diederich et al. ................. | 601/3 |
| 8,081,925 B2 * | 12/2011 | Parramon et al. ............. | 455/41.1 |
| 8,175,677 B2 * | 5/2012 | Sayler et al. ................... | 600/417 |
| 8,208,993 B2 * | 6/2012 | Piferi et al. .................... | 600/426 |
| 8,340,743 B2 * | 12/2012 | Jenkins et al. ................ | 600/429 |
| 8,374,677 B2 * | 2/2013 | Piferi et al. .................... | 600/417 |
| 8,467,864 B2 * | 6/2013 | Park .............................. | 600/513 |
| 2002/0045816 A1 | 4/2002 | Atalar et al. | |
| 2004/0199069 A1 * | 10/2004 | Connelly et al. .............. | 600/412 |
| 2007/0238975 A1 | 10/2007 | Zeijlemaker | |

(Continued)

FOREIGN PATENT DOCUMENTS

DE        600 17 074 T2    3/2006
DE        103 14 215 B4    11/2006
WO     WO 2007/064739 A2    6/2007

OTHER PUBLICATIONS

German Office Action dated Jan. 31, 2013, for corresponding German Patent Application No. DE 10 2010 020 152.9 with English translation.

(Continued)

*Primary Examiner* — Brij Shrivastav
(74) *Attorney, Agent, or Firm* — Lempia Summerfield Katz LLC

(57) ABSTRACT

The present embodiments relate to an apparatus that includes a local coil for a magnetic resonance tomography system and an implantable device.

30 Claims, 1 Drawing Sheet

(56) References Cited

U.S. PATENT DOCUMENTS

| | | | |
|---|---|---|---|
| 2008/0262584 A1 | 10/2008 | Bottomley et al. | |
| 2009/0118610 A1* | 5/2009 | Karmarkar et al. | 600/420 |
| 2009/0149933 A1 | 6/2009 | Ameri | |
| 2011/0288403 A1* | 11/2011 | Kondabatni et al. | 600/421 |

OTHER PUBLICATIONS

German Office Action dated Jan. 21, 2011 for corresponding German Patent Application No. DE 10 2010 020 152.9-54 with English translation.

* cited by examiner

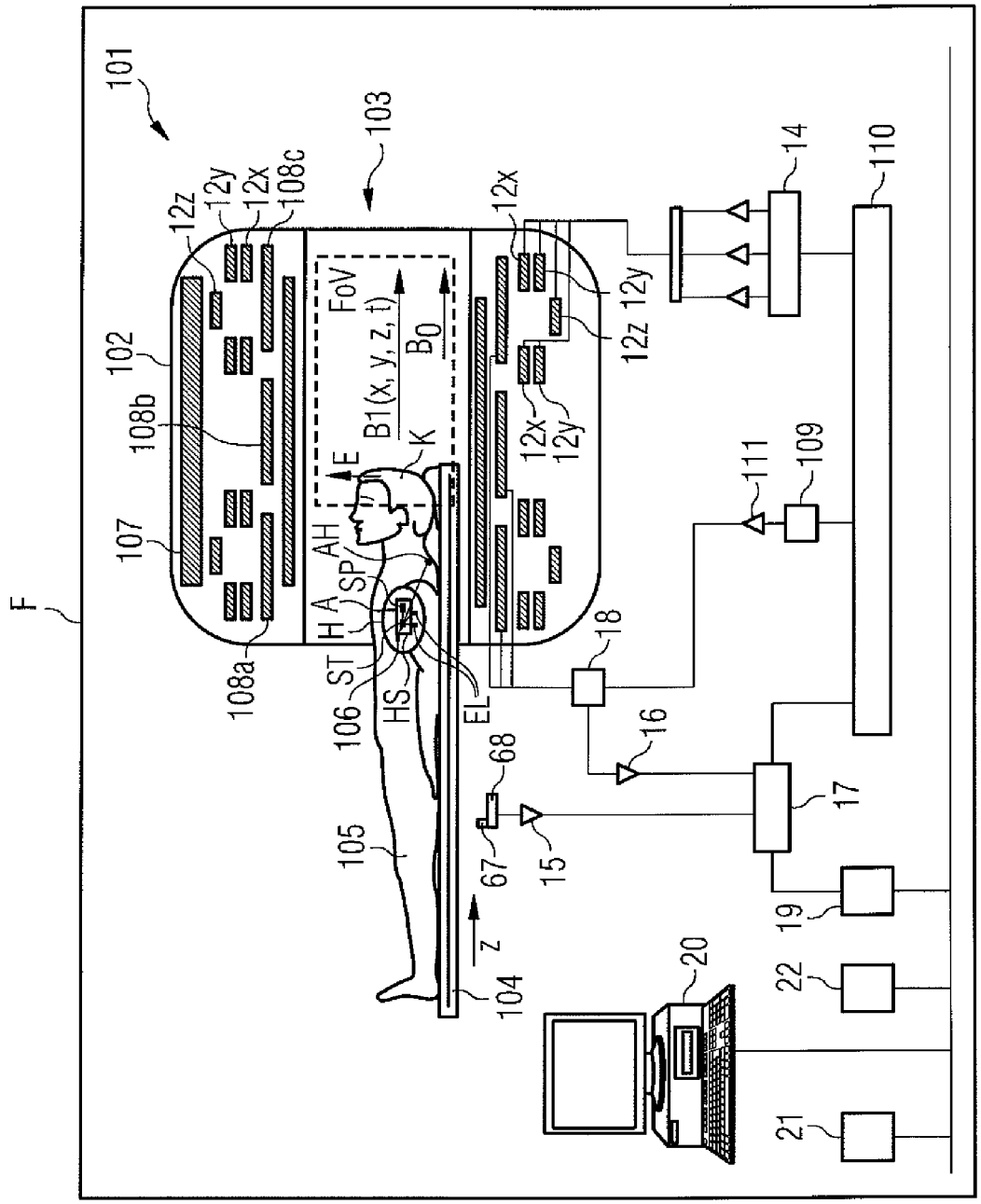

APPARATUS WITH LOCAL COIL ARRANGEMENT AND IMPLANTABLE DEVICE

This application claims the benefit of DE 10 2010 020 152.9, filed May 11, 2010.

BACKGROUND

The present embodiments relate to a local coil arrangement for a magnetic resonance tomography system.

Magnetic resonance tomography devices for examining, for example, patients using magnetic resonance tomography are known from DE10314215B4.

In MR tomography, signals are recorded using local coils (e.g., loops). Excited nuclei of an examination subject (e.g., a patient) induce a voltage by way of radiation emitted by the excited nuclei in a local coil antenna receiving the radiation as a signal. The induced voltage is amplified by a low-noise preamplifier (LNA) and forwarded to receive electronics of a magnetic resonance tomography (MRT) system.

In order to examine patients fitted with cardiac pacemakers, some of whom are suffering from illnesses such as, for example, cardiac arrhythmia, heart failure or coronary diseases, use is made of, for example, imaging methods based on ionizing beams such as SPECT, X-ray fluoroscopy or CT.

MRT may also be employed for assessing cardiac performance and cardiac perfusion. MRT may be limited in terms of the speed of imaging. This may constitute a problem for the heart, for example, which is in motion due to heartbeat and respiration.

US 20090149933, US 20080262584 and US 20070238975 describe MR-compatible cardiac pacemakers that operate in the magnetic field of an MRT system and are designed in such a way that risks (e.g., due to the heating of pacemakers or electrodes) are excluded. Receive coils (e.g., arrays) that are placed onto the chest of the patient or positioned under the patient are used for imaging. Cardiac pacemakers have a negative effect on image quality because the cardiac pacemaker generate artifacts. Catheters from the company Topspin Medical as disclosed in U.S. Pat. No. 6,600,319 or from Surgi-Vision as disclosed in US 20020045816 are also known for conducting catheter examinations.

SUMMARY AND DESCRIPTION

The present embodiments may obviate one or more the drawbacks or limitations in the related art. For example, an MRT local coil may be optimized.

The present embodiments include a local coil with a cardiac pacemaker.

An advantage may lie, for example, in simple follow-up investigations with high image quality.

BRIEF DESCRIPTION OF THE DRAWINGS

FIG. 1 shows an MRT system and one embodiment of a local coil.

DETAILED DESCRIPTION OF THE DRAWINGS

FIG. 1 shows an imaging magnetic resonance device MRT 101 (in a room isolated by a Faraday cage F) having a whole-body coil 102 with a tubular or laterally open examination subject bore 103 (enclosing a field of view FoV of the MRT 101, for example, at top and bottom using a housing wall). A patient couch 104 (e.g., a patient bed) supporting an examination subject such as, for example, a patient 105 (e.g., with a local coil arrangement 106) may be moved into the examination subject bore 103 in the direction of the arrow z in order to generate images of the patient 105. In one embodiment, a local coil arrangement 106, for acquiring images of a local region (e.g., the head K) when the patient 105 is moved in the direction z into the field of view FoV may be placed on the patient 105. Received signals may be transmitted by the local coil arrangement 106 via, for example, coaxial cable or radio link (e.g., via antennas A, 67) to a component 67, 66, 15, 17 of the MRT 101 (e.g., an evaluation entity) and evaluated by the component (e.g., converted into images and stored or displayed).

In order to examine the body 105 (e.g., the examination subject or the patient) using the magnetic resonance device MRT 101 using magnetic resonance imaging, different magnetic fields that are coordinated with one another in terms of temporal and spatial characteristics are applied to the body 105. A strong magnet (e.g., a cryomagnet 107 in a measurement chamber having a tunnel-shaped bore 3) generates a strong static main magnetic field $B_0$ in the range from, for example, 0.2 Tesla to 3 Tesla or more. The body 105 that is to be examined is positioned on the patient couch 104 and is moved into a region of the main magnetic field $B_0$ that is approximately homogeneous in the field of view FoV. The nuclear spins of atomic nuclei of the body 105 are excited via magnetic radio-frequency excitation pulses that are transmitted via a radio-frequency antenna shown in FIG. 1 in simplified form as a body coil 108 (e.g., and/or possibly a local coil arrangement). Radio-frequency excitation pulses are generated, for example, by a pulse generation unit 109 that is controlled by a pulse sequence control unit 110. After being amplified using a radio-frequency amplifier 111, the radio-frequency excitation pulses are routed to the radio-frequency antenna 108 a, b, c. The radio-frequency system shown in FIG. 1 is only shown schematically. In other embodiments, more than one pulse generation unit 109, more than one radio-frequency amplifier 111 and a plurality of radio-frequency antennas 108 a, b, c are used in the imaging magnetic resonance device MRT 101.

The imaging magnetic resonance device MRT 101 also includes gradient coils 12x, 12y, 12z for radiating magnetic gradient fields in the course of a measurement in order to produce selective layer excitation and for spatial encoding of the measurement signal. The gradient coils 12x, 12y, 12z are controlled by a gradient coil control unit 14 that, like the pulse generation unit 109, is connected to the pulse sequence control unit 110.

The signals emitted by the excited nuclear spins are received by a single-part or, as shown in FIG. 1, a multipart body coil 108a, 108b, 108c and/or at least one local coil arrangement 106, amplified by associated radio-frequency preamplifiers 16, transmitted in analog or digitized form, and processed further and digitized by a receiving unit 17. The recorded measured data is stored in digitized form as complex numeric values in a k-space matrix. An associated MR image of the examination subject may be reconstructed using a multidimensional Fourier transform from the k-space matrix populated with values.

For a coil that may be operated both in transmit and in receive mode such as, for example, the body coil 108a, b, c, and/or the local coil 106, correct signal forwarding is controlled using an upstream-connected duplexer 18.

From the measured data, an image processing unit 19 generates an image that is displayed to a user via an operator console 20 and/or stored in a memory unit 21. A central computer unit 22 controls the individual system components.

In some MR tomography procedures, images having a high signal-to-noise ratio (SNR) may be recorded using local coil arrangements (e.g., loops, local coils). The local coil arrangements (e.g., antenna systems) are disposed in the immediate vicinity of the examination subject on (anterior) or under (posterior) or in the body 105. In the course of an MR measurement, the excited nuclei induce a voltage in the individual antennas of the local coil 106. The induced voltage is amplified by a low-noise preamplifier (e.g., LNA, preamp) and forwarded to receive electronics. High-field systems (e.g., 1.5 T or 3 T and more) are also used in the case of high-resolution images in order to improve the signal-to-noise ratio. Since more individual antennas may be connected to an MR receiving system than there are receivers present, a switching array (e.g., RCCS) is installed between the receive antennas and the receivers. The switching array routes the currently active receive channels (e.g., the receive channels currently lying in the field of view of the magnet) to the receivers present. This enables more coil elements to be connected than there are receivers present, since in the case of whole-body coverage, only the coils that are located in the field of view FoV or in the homogeneity volume of the magnet are to be read out.

The local coil arrangement 106 (e.g., a local coil system) may include, for example, one antenna element or a plurality of antenna elements (e.g., coil elements) configured as an array coil. A local coil system 106 may include, for example, coil elements, a preamplifier, further electronics, a housing, supports, and a radio link or a cable with plug, by which, the local coil system 106 is connected to the imaging magnetic resonance device MRT 101. A receiver 68 mounted on the system side filters and (for analog transmission) digitizes signals received, for example, wirelessly or via cable by the local coil 106 and passes the data to a digital signal processing device. The digital signal processing device may derive an image or a spectrum from the data acquired using a measurement and makes the image or the spectrum available to a user, for example, for subsequent diagnosis by the user or for storage in a memory.

Several exemplary embodiments are described in more detail below.

A magnetic resonance tomography local coil 106 of a magnetic resonance tomography (MRT) system 101 is connected via radio link to an evaluation device (e.g., elements 67, 66, 15, 17) of the magnetic resonance tomography system 101.

MRT signals E transmitted as radio-frequency radiation by nuclei of an examination subject (e.g., a patient) 105 are received by one or more antennas EL, A of the local coil 106, stored (SP) and/or amplified by at least one preamplifier 30 in or on the local coil 106 and transferred in analog or digitized form using an antenna A; EL to the evaluation entity (e.g., elements 67, 66, 15, 17) of the magnetic resonance tomography system 101.

According to the present embodiments, the local coil 106 is disposed, for example, on or in an implantable device (e.g., a cardiac pacemaker HS in the heart H of the patient) or fully or partially contains the implantable device HS. The local coil 106 (e.g., a controller ST of the local coil 106) may be connected, for example, to an electrode ES (indicated schematically in FIG. 1) of the cardiac pacemaker HS via a lead.

In one embodiment, a combined cardiac pacemaker and MR receiving system (e.g., a combined system) is provided.

The combined system enables MR signals to be received directly from the immediate vicinity of the heart with a high signal-to-noise ratio.

The local coil 106 (e.g., a local coil system or a local coil/cardiac pacemaker system) transmits MRT signals wirelessly (e.g., by radio or by microwaves), for example, via an antenna A (e.g., where a housing or the electrodes of the cardiac pacemaker may also be used as the antenna A) of the cardiac pacemaker HS to an antenna 67 of a receiving entity (e.g., a receiving device) of the MRT 101. Alternatively or additionally, the local coil 106 stores MRT signals in digitized form (so that at some point the MRT signals may be read out using a trigger signal in a wired manner) in a memory SP in the cardiac pacemaker/local coil system.

Cardiac pacemakers, cardiac pacemaker electrodes and cardiac pacemaker transmit antennas may be known to the person skilled, so they are not described in detail here.

In one embodiment, the cardiac pacemaker HS includes at least one receive coil and processing and digitizing electronics ST. The data E is transmitted in digital form, either in real-time via a radio link, or the data is stored locally in the system and transferred with a delay (e.g., outside of the MRT).

In another embodiment, the local coil 106 may be inductively coupled.

In one embodiment, the system (e.g., the cardiac pacemaker HS and the local coil 106) uses, for example, a microwave system such as described in U.S. Pat. No. 7,417,433, for transferring the measured data from the local coil 106 to the MRT system 101.

In one embodiment, for data E that is to be transferred from the local coil 106 to the MRT system 101, the system may possess a separate transmit antenna All that is implanted, for example, directly under the skin.

In addition to the received MR data, the system may transmit physiological information to the MRT system (e.g., an ECG signal that may be used for triggering).

In one embodiment, the system may transmit information used for retrospectively discarding measured MR data E acquired during atypical physiological states (e.g., during a defibrillation using an implantable cardioverter/defibrillator).

The system may transfer data used for avoiding interactions (e.g., the temperature of parts of the cardiac pacemaker HS) to the MR system. The MR system may automatically adjust the imaging parameters (e.g., RF power) as a function of the transferred data.

The MR system may transfer data to the cardiac pacemaker HS and modify programming of the cardiac pacemaker HS (e.g., in order to select a lower heart rate temporarily or to coordinate cardiac activity with the pulse sequence used).

In one embodiment, electrodes EL of the cardiac pacemaker HS may be used to receive the MR signal E. In the process, a motion correction may also be derived, for example, from the detuning of the electrodes EL taking place due to the cardiac and respiratory movement.

In one embodiment, the cardiac pacemaker HS may be, for example, an implantable cardioverter/defibrillator (ICD), a CRT or a CRT-D.

In the example described, the device that is implantable as an implant in a human being is a cardiac pacemaker HS. Alternatively, the implantable device may be any other implantable device (e.g., that may be introduced as an implant into a human being), such as, for example, an insulin pump, an artificial joint, a gastrological replacement part or a vascular implant.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An apparatus comprising:
   a local coil for a magnetic resonance tomography system; and
   an implantable device electrically connected to the local coil,
   wherein the implantable device comprises a cardiac pacemaker, and
   wherein the local coil is integrated in the implantable device.

2. The apparatus as claimed in claim 1, wherein the implantable device comprises a device for electrically stimulating tissue.

3. The apparatus as claimed in claim 1, wherein the implantable device comprises a brain pacemaker, a deep brain stimulator, or a spinal cord stimulator.

4. The apparatus as claimed in claim 1, wherein the local coil is mechanically connected to the implantable device.

5. The apparatus as claimed in claim 1,
   wherein the local coil is physically contained at least in part in the cardiac pacemaker.

6. The apparatus as claimed in claim 1, wherein the local coil is electrically connected to a controller of the implantable device.

7. The apparatus as claimed in claim 1, further comprising a controller that controls the local coil and the implantable device,
   wherein the controller is connected to the local coil and the implantable device for controlling actuation of the local coil and the implantable device.

8. The apparatus as claimed in claim 1,
   wherein the local coil is mechanically connected to an electrode of the cardiac pacemaker.

9. The apparatus as claimed in claim 8, wherein the local coil is electrically connected to the electrode of the cardiac pacemaker using a lead.

10. The apparatus as claimed in claim 1, wherein the local coil comprises an antenna, the antenna configured for wirelessly transmitting signals to a magnetic resonance tomography (MRT) system for evaluation of the transmitted signals at the MRT system.

11. The apparatus as claimed in claim 1, wherein the local coil comprises a magnetic resonance tomography (MRT) receive coil, the MRT receive coil configured for receiving signals emitted by atomic nuclei of an examination subject situated in an MRT system.

12. The apparatus as claimed in claim 1, wherein the local coil comprises a controller having processing, digitizing, or processing and digitizing electronics for magnetic resonance tomography (MRT) signals received from an examination subject in an MRT system.

13. The apparatus as claimed in claim 1, wherein the local coil comprises a transmitting device, the transmitting device configured for digitally transmitting digitized signals.

14. The apparatus as claimed in claim 1, wherein the local coil comprises:
   a controller having digitizing electronics, the digitizing electronics configured for digitizing MRT signals received from an examination subject in an MRT system; and
   a memory configured for storing the received digitized MRT signals.

15. The apparatus as claimed in claim 14, wherein the controller is configured for time-delayed transmission of the received digitized MRT signals stored in the memory.

16. The apparatus as claimed in claim 1, wherein the local coil comprises an induction transmitting device, the induction transmitting device configured for transmitting data to a receiving device inside or outside of an magnetic resonance tomography system.

17. The apparatus as claimed in claim 1, wherein the local coil comprises a microwave transmitting device, the microwave transmitting device configured for transmitting data to a receiving device of a magnetic resonance tomography device.

18. The apparatus as claimed in claim 1, wherein the local coil comprises a transmitting device or an antenna, the transmitting device or the antenna being implantable under the skin of a patient and being configured for transmitting data to a receiving device of a magnetic resonance tomography system.

19. The apparatus as claimed in claim 1, wherein the local coil comprises a transmitting device, the transmitting device configured for transmitting physiological information to a receiving device of a magnetic resonance tomography system.

20. The apparatus as claimed in claim 1, wherein the local coil is configured for transmitting an ECG signal.

21. The apparatus as claimed in claim 1, wherein the local coil comprises a receiving device, and
   wherein the local coil is induced to transmit data by a trigger signal that is receivable via the receiving device.

22. The apparatus as claimed in claim 21, wherein the local coil is induced to delete stored data by a delete signal that is received via the receiving device, the stored data being data measured by an implantable cardioverter/defibrillator during a defibrillation or other physiological states.

23. The apparatus as claimed in claim 1, wherein the local coil comprises a receiving device,
   wherein the local coil is controllable by a cardiac pacemaker control signal that is receivable by the receiving device for controlling the cardiac pacemaker, the controlling comprising temporarily setting the cardiac pacemaker to a lower heart rate specifiable to a heart or coordinating, using the cardiac pacemaker, a cardiac activity with a pulse sequence used by a magnetic resonance tomography system.

24. The apparatus as claimed in claim 1, wherein the apparatus is connected to cardiac pacemaker electrodes of a cardiac pacemaker, the apparatus being configured to receive a radio-frequency magnetic resonance signal emitted by an examination subject via the cardiac pacemaker electrodes.

25. The apparatus as claimed in claim 24, wherein the cardiac pacemaker comprises an implantable cardioverter, a defibrillator, or an implantable cardioverter and defibrillator, a cardiac resynchronization therapy device, or a cardiac resynchronization therapy defibrillator.

26. The apparatus as claimed in claim 1, wherein the local coil comprises a magnetic resonance tomography local coil.

27. The apparatus as claimed in claim 1, wherein the local coil is only a receive coil for analog magnetic resonance tomography signals.

28. The apparatus as claimed in claim 1, wherein the local coil is a receive coil and a transmit coil for analog magnetic resonance tomography signals.

29. The apparatus as claimed in claim 1, wherein the local coil comprises only one antenna for magnetic resonance tomography signals.

30. The apparatus as claimed in claim 1, wherein the local coil comprises a plurality of antenna for magnetic resonance tomography signals.

\* \* \* \* \*